US008114394B2

(12) United States Patent
Vicary et al.

(10) Patent No.: US 8,114,394 B2
(45) **Date of Patent: *Feb. 14, 2012**

(54) USE OF IL-1 ANTAGONISTS TO TREAT GOUT

(75) Inventors: Catherine Vicary, New York, NY (US); Scott Mellis, New Rochelle, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/887,529

(22) Filed: Sep. 22, 2010

(65) Prior Publication Data

US 2011/0008374 A1 Jan. 13, 2011

Related U.S. Application Data

(63) Continuation of application No. 12/567,816, filed on Sep. 28, 2009, now Pat. No. 7,820,154, which is a continuation of application No. 12/200,681, filed on Aug. 28, 2008, now Pat. No. 7,632,490, which is a continuation-in-part of application No. 11/975,593, filed on Oct. 19, 2007, now abandoned.

(60) Provisional application No. 60/853,385, filed on Oct. 20, 2006.

(51) Int. Cl.

| | |
|---|---|
| ***A61K 38/03*** | (2006.01) |
| *A61K 38/16* | (2006.01) |
| *A61K 38/44* | (2006.01) |
| *A61K 31/195* | (2006.01) |

(52) U.S. Cl. ..................... 424/85.1; 424/94.4; 514/12.2; 514/16.7

(58) Field of Classification Search ........................ None
See application file for complete search history.

(56) References Cited

U.S. PATENT DOCUMENTS

| | | | | |
|---|---|---|---|---|
| 6,472,179 | B2 | 10/2002 | Stahl et al. | |
| 6,927,044 | B2 | 8/2005 | Stahl et al. | |
| 7,632,490 | B2 * | 12/2009 | Vicary et al. | 424/85.1 |
| 7,820,154 | B2 * | 10/2010 | Vicary et al. | 424/85.1 |
| 2005/0129685 | A1 | 6/2005 | Cao et al. | |
| 2005/0197293 | A1 | 9/2005 | Mellis et al. | |
| 2007/0161559 | A1 | 7/2007 | Petrilli et al. | |

FOREIGN PATENT DOCUMENTS

| | | | |
|---|---|---|---|
| WO | WO 2004/100987 | A1 | 11/2004 |
| WO | WO 2005/117945 | A1 | 12/2005 |
| WO | WO 2006/084145 | A1 | 8/2006 |
| WO | WO 2007/077042 | A1 | 7/2007 |
| WO | WO 2007/077261 | A1 | 7/2007 |

OTHER PUBLICATIONS

Martinon, 2006, "Gout-associated uric acid crystals activate the NALP3 inflammasome," Nature 440:237-241 (Nature Publishing Group, London, UK).

Gabay, 2003, "IL-1 Trap," Curr. Opin. Invest. Drugs 4:593-597 (Thompson Reuters, Philadelphia, PA).

Hashizume et al., 1989, "A role of interleukin-1 (IL-1) in crystal-induced arthritis," Adv. Exp. Med. Biol. 253a:219-224 (Kluwer Academic/Plenum Publishers, New York, NY).

Takahashi et al., 2003, "Effects of combination treatment using anti-hyperuricaemic agents with fenofibrate and/or losartan . . . " Ann. Rheum. Dis. 62:572-575 (BMJ, London, UK).

Schlesinger, 2004, "Managment of acute and chronic gouty arthritis, present state of the art," Drugs 64:2399-2416 (Adis Press, Auckland, NZ).

* cited by examiner

*Primary Examiner* — Bridget E Bunner
*Assistant Examiner* — Fozia Hamud
(74) *Attorney, Agent, or Firm* — Valeta Gregg, Esq.; Frank R. Cottingham, Esq.

(57) ABSTRACT

Methods of treating, inhibiting, or ameliorating gout, including chronic acute (refractory) gout, pseudogout, or drug-induced gout, in a human subject in need thereof, comprising administering to a subject in need a therapeutic amount of an interleukin 1 (IL-1) antagonist, wherein the incidence of a gout flare is reduced or inhibited.

20 Claims, No Drawings

SEQUENCE LISTING

```
<160> NUMBER OF SEQ ID NOS: 26

<210> SEQ ID NO 1
<211> LENGTH: 2733
<212> TYPE: DNA
<213> ORGANISM: Homo sapiens

<400> SEQUENCE: 1

atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240
```

-continued

```
gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtgtccggt   1080
ggcgcgccta tgctgagcga ggctgataaa tgcaaggaac gtgaagaaaa aataatttta   1140
gtgtcatctg caaatgaaat tgatgttcgt ccctgtcctc ttaacccaaa tgaacacaaa   1200
ggcactataa cttggtataa ggatgacagc aagacacctg tatctacaga acaagcctcc   1260
aggattcatc aacacaaaga gaaactttgg tttgttcctg ctaaggtgga ggattcagga   1320
cattactatt gcgtggtaag aaattcatct tactgcctca gaattaaaat aagtgcaaaa   1380
tttgtggaga atgagcctaa cttatgttat aatgcacaag ccatatttaa gcagaaacta   1440
cccgttgcag gagacggagg acttgtgtgc ccttatatgg agttttttaa aaatgaaaat   1500
aatgagttac ctaaattaca gtggtataag gattgcaaac ctctacttct tgacaatata   1560
cactttagtg gagtcaaaga taggctcatc gtgatgaatg tggctgaaaa gcatagaggg   1620
aactatactt gtcatgcatc ctacacatac ttgggcaagc aatatcctat tacccgggta   1680
atagaattta ttactctaga ggaaaacaaa cccacaaggc ctgtgattgt gagcccagct   1740
aatgagacaa tggaagtaga cttgggatcc cagatacaat tgatctgtaa tgtcaccggc   1800
cagttgagtg acattgctta ctggaagtgg aatgggtcag taattgatga agatgaccca   1860
gtgctagggg aagactatta cagtgtggaa aatcctgcaa acaaaaagaag gagtaccctc  1920
atcacagtgc ttaatatatc ggaaattgag agtagatttt ataaacatcc atttacctgt   1980
tttgccaaga atacacatgg tatagatgca gcatatatcc agttaatata tccagtcact   2040
aattccggag acaaaactca cacatgccca ccgtgcccag cacctgaact cctgggggga   2100
ccgtcagtct tcctcttccc cccaaaaccc aaggacaccc tcatgatctc ccggacccct   2160
gaggtcacat gcgtggtggt ggacgtgagc cacgaagacc ctgaggtcaa gttcaactgg   2220
tacgtggacg gcgtggaggt gcataatgcc aagacaaagc cgcgggagga gcagtacaac   2280
agcacgtacc gtgtggtcag cgtcctcacc gtcctgcacc aggactggct gaatggcaag   2340
gagtacaagt gcaaggtctc caacaaagcc ctcccagccc ccatcgagaa aaccatctcc   2400
aaagccaaag ggcagccccg agaaccacag gtgtacaccc tgcccccatc ccgggaggag   2460
atgaccaaga accaggtcag cctgacctgc ctggtcaaag gcttctatcc cagcgacatc   2520
gccgtggagt gggagagcaa tgggcagccg gagaacaact acaagaccac gcctcccgtg   2580
ctggactccg acggctcctt cttcctctat agcaagctca ccgtggacaa gagcaggtgg   2640
```

```
cagcagggga acgtcttctc atgctccgtg atgcatgagg ctctgcacaa ccactacacg   2700

cagaagagcc tctccctgtc tccgggtaaa tga                                2733


<210> SEQ ID NO 2
<211> LENGTH: 910
<212> TYPE: PRT
<213> ORGANISM: Homo sapiens

<400> SEQUENCE: 2

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Ser Gly Gly Ala Pro Met Leu Ser Glu Ala
        355                 360                 365
```

```
Asp Lys Cys Lys Glu Arg Glu Glu Lys Ile Ile Leu Val Ser Ser Ala
    370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
            420                 425                 430

Pro Ala Lys Val Glu Asp Ser Gly His Tyr Tyr Cys Val Val Arg Asn
        435                 440                 445

Ser Ser Tyr Cys Leu Arg Ile Lys Ile Ser Ala Lys Phe Val Glu Asn
    450                 455                 460

Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
                485                 490                 495

Lys Asn Glu Asn Asn Glu Leu Pro Lys Leu Gln Trp Tyr Lys Asp Cys
            500                 505                 510

Lys Pro Leu Leu Leu Asp Asn Ile His Phe Ser Gly Val Lys Asp Arg
        515                 520                 525

Leu Ile Val Met Asn Val Ala Glu Lys His Arg Gly Asn Tyr Thr Cys
    530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
            580                 585                 590

Gln Leu Ile Cys Asn Val Thr Gly Gln Leu Ser Asp Ile Ala Tyr Trp
        595                 600                 605

Lys Trp Asn Gly Ser Val Ile Asp Glu Asp Asp Pro Val Leu Gly Glu
    610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
            660                 665                 670

Ile Gln Leu Ile Tyr Pro Val Thr Asn Ser Gly Asp Lys Thr His Thr
        675                 680                 685

Cys Pro Pro Cys Pro Ala Pro Glu Leu Leu Gly Gly Pro Ser Val Phe
    690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
                725                 730                 735

Lys Phe Asn Trp Tyr Val Asp Gly Val Glu Val His Asn Ala Lys Thr
            740                 745                 750

Lys Pro Arg Glu Glu Gln Tyr Asn Ser Thr Tyr Arg Val Val Ser Val
        755                 760                 765

Leu Thr Val Leu His Gln Asp Trp Leu Asn Gly Lys Glu Tyr Lys Cys
    770                 775                 780

Lys Val Ser Asn Lys Ala Leu Pro Ala Pro Ile Glu Lys Thr Ile Ser
```

```
785                 790                 795                 800

Lys Ala Lys Gly Gln Pro Arg Glu Pro Gln Val Tyr Thr Leu Pro Pro
                805                 810                 815

Ser Arg Glu Glu Met Thr Lys Asn Gln Val Ser Leu Thr Cys Leu Val
            820                 825                 830

Lys Gly Phe Tyr Pro Ser Asp Ile Ala Val Glu Trp Glu Ser Asn Gly
        835                 840                 845

Gln Pro Glu Asn Asn Tyr Lys Thr Thr Pro Pro Val Leu Asp Ser Asp
    850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
            900                 905                 910


<210> SEQ ID NO 3
<211> LENGTH: 2703
<212> TYPE: DNA
<213> ORGANISM: Homo sapiens

<400> SEQUENCE: 3

atggtgttac tcagacttat ttgtttcata gctctactga tttcttctct ggaggctgat      60

aaatgcaagg aacgtgaaga aaaaataatt ttagtgtcat ctgcaaatga aattgatgtt     120

cgtccctgtc ctcttaaccc aaatgaacac aaaggcacta taacttggta taaggatgac     180

agcaagacac ctgtatctac agaacaagcc tccaggattc atcaacacaa agagaaactt     240

tggtttgttc ctgctaaggt ggaggattca ggacattact attgcgtggt aagaaattca     300

tcttactgcc tcagaattaa aataagtgca aaatttgtgg agaatgagcc taacttatgt     360

tataatgcac aagccatatt taagcagaaa ctacccgttg caggagacgg aggacttgtg     420

tgcccttata tggagttttt taaaaatgaa aataatgagt tacctaaatt acagtggtat     480

aaggattgca aacctctact tcttgacaat atacacttta gtggagtcaa agataggctc     540

atcgtgatga atgtggctga aaagcataga gggaactata cttgtcatgc atcctacaca     600

tacttgggca agcaatatcc tattacccgg gtaatagaat ttattactct agaggaaaac     660

aaacccacaa ggcctgtgat tgtgagccca gctaatgaga caatggaagt agacttggga     720

tcccagatac aattgatctg taatgtcacc ggccagttga gtgacattgc ttactggaag     780

tggaatgggt cagtaattga tgaagatgac ccagtgctag gggaagacta ttacagtgtg     840

gaaaatcctg caaacaaaag aaggagtacc ctcatcacag tgcttaatat atcggaaatt     900

gagagtagat tttataaaca tccatttacc tgttttgcca agaatacaca tggtatagat     960

gcagcatata tccagttaat atatccagtc actaattcag aacgctgcga tgactgggga    1020

ctagacacca tgaggcaaat ccaagtgttt gaagatgagc cagctcgcat caagtgccca    1080

ctctttgaac acttcttgaa attcaactac agcacagccc attcagctgg ccttactctg    1140

atctggtatt ggactaggca ggaccgggac cttgaggagc caattaactt ccgcctcccc    1200

gagaaccgca ttagtaagga gaaagatgtg ctgtggttcc ggcccactct cctcaatgac    1260

actggcaact atacctgcat gttaaggaac actacatatt gcagcaaagt tgcatttccc    1320

ttggaagttg ttcaaaaaga cagctgtttc aattccccca tgaaactccc agtgcataaa    1380

ctgtatatag aatatggcat tcagaggatc acttgtccaa atgtagatgg atattttcct    1440

tccagtgtca aaccgactat cacttggtat atgggctgtt ataaaataca gaattttaat    1500
```

```
aatgtaatac ccgaaggtat gaacttgagt ttcctcattg ccttaatttc aaataatgga   1560

aattacacat gtgttgttac atatccagaa aatggacgta cgtttcatct caccaggact   1620

ctgactgtaa aggtagtagg ctctccaaaa aatgcagtgc cccctgtgat ccattcacct   1680

aatgatcatg tggtctatga gaaagaacca ggagaggagc tactcattcc ctgtacggtc   1740

tattttagtt ttctgatgga ttctcgcaat gaggtttggt ggaccattga tggaaaaaaa   1800

cctgatgaca tcactattga tgtcaccatt aacgaaagta taagtcatag tagaacagaa   1860

gatgaaacaa gaactcagat tttgagcatc aagaaagtta cctctgagga tctcaagcgc   1920

agctatgtct gtcatgctag aagtgccaaa ggcgaagttg ccaaagcagc caaggtgaag   1980

cagaaagtgc cagctccaag atacacagtg gaatccggag acaaaactca cacatgccca   2040

ccgtgcccag cacctgaact cctgggggga ccgtcagtct tcctcttccc cccaaaaccc   2100

aaggacaccc tcatgatctc ccggacccct gaggtcacat gcgtggtggt ggacgtgagc   2160

cacgaagacc ctgaggtcaa gttcaactgg tacgtggacg gcgtggaggt gcataatgcc   2220

aagacaaagc cgcgggagga gcagtacaac agcacgtacc gtgtggtcag cgtcctcacc   2280

gtcctgcacc aggactggct gaatggcaag gagtacaagt gcaaggtctc caacaaagcc   2340

ctcccagccc ccatcgagaa aaccatctcc aaagccaaag ggcagccccg agaaccacag   2400

gtgtacaccc tgcccccatc ccgggaggag atgaccaaga accaggtcag cctgacctgc   2460

ctggtcaaag gcttctatcc cagcgacatc gccgtggagt gggagagcaa tgggcagccg   2520

gagaacaact acaagaccac gcctcccgtg ctggactccg acggctcctt cttcctctat   2580

agcaagctca ccgtggacaa gagcaggtgg cagcagggga acgtcttctc atgctccgtg   2640

atgcatgagg ctctgcacaa ccactacacg cagaagagcc tctccctgtc tccgggtaaa   2700

tga                                                                 2703
```

```
<210> SEQ ID NO 4
<211> LENGTH: 900
<212> TYPE: PRT
<213> ORGANISM: Homo sapiens

<400> SEQUENCE: 4

Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160
```

```
Lys Asp Cys Lys Pro Leu Leu Leu Asp Asn Ile His Phe Ser Gly Val
            165                 170                 175

Lys Asp Arg Leu Ile Val Met Asn Val Ala Glu Lys His Arg Gly Asn
        180                 185                 190

Tyr Thr Cys His Ala Ser Tyr Thr Tyr Leu Gly Lys Gln Tyr Pro Ile
    195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
            245                 250                 255

Ala Tyr Trp Lys Trp Asn Gly Ser Val Ile Asp Glu Asp Asp Pro Val
        260                 265                 270

Leu Gly Glu Asp Tyr Tyr Ser Val Glu Asn Pro Ala Asn Lys Arg Arg
    275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
            325                 330                 335

Asp Asp Trp Gly Leu Asp Thr Met Arg Gln Ile Gln Val Phe Glu Asp
        340                 345                 350

Glu Pro Ala Arg Ile Lys Cys Pro Leu Phe Glu His Phe Leu Lys Phe
    355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
            405                 410                 415

Leu Leu Asn Asp Thr Gly Asn Tyr Thr Cys Met Leu Arg Asn Thr Thr
        420                 425                 430

Tyr Cys Ser Lys Val Ala Phe Pro Leu Glu Val Val Gln Lys Asp Ser
    435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
            485                 490                 495

Gln Asn Phe Asn Asn Val Ile Pro Glu Gly Met Asn Leu Ser Phe Leu
        500                 505                 510

Ile Ala Leu Ile Ser Asn Asn Gly Asn Tyr Thr Cys Val Val Thr Tyr
    515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
            565                 570                 575

Pro Cys Thr Val Tyr Phe Ser Phe Leu Met Asp Ser Arg Asn Glu Val
```

-continued

```
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Asp Lys Thr His Thr Cys Pro Pro Cys Pro Ala Pro Glu Leu Leu
        675                 680                 685

Gly Gly Pro Ser Val Phe Leu Phe Pro Pro Lys Pro Lys Asp Thr Leu
    690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
        755                 760                 765

Gly Lys Glu Tyr Lys Cys Lys Val Ser Asn Lys Ala Leu Pro Ala Pro
    770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Glu Glu Met Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900


<210> SEQ ID NO 5
<211> LENGTH: 2709
<212> TYPE: DNA
<213> ORGANISM: Homo sapiens

<400> SEQUENCE: 5

atggtgttac tcagacttat ttgtttcata gctctactga tttcttctct ggaggctgat      60

aaatgcaagg aacgtgaaga aaaaataatt ttagtgtcat ctgcaaatga aattgatgtt     120

cgtccctgtc ctcttaaccc aaatgaacac aaaggcacta taacttggta taaggatgac     180

agcaagacac ctgtatctac agaacaagcc tccaggattc atcaacacaa agagaaactt     240

tggtttgttc ctgctaaggt ggaggattca ggacattact attgcgtggt aagaaattca     300
```

```
tcttactgcc tcagaattaa aataagtgca aaatttgtgg agaatgagcc taacttatgt    360
tataatgcac aagccatatt taagcagaaa ctacccgttg caggagacgg aggacttgtg    420
tgcccttata tggagttttt taaaaatgaa aataatgagt tacctaaatt acagtggtat    480
aaggattgca aacctctact tcttgacaat atacacttta gtggagtcaa agataggctc    540
atcgtgatga atgtggctga aaagcataga gggaactata cttgtcatgc atcctacaca    600
tacttgggca agcaatatcc tattacccgg gtaatagaat ttattactct agaggaaaac    660
aaacccacaa ggcctgtgat tgtgagccca gctaatgaga caatggaagt agacttggga    720
tcccagatac aattgatctg taatgtcacc ggccagttga gtgacattgc ttactggaag    780
tggaatgggt cagtaattga tgaagatgac ccagtgctag gggaagacta ttacagtgtg    840
gaaaatcctg caaacaaaag aaggagtacc ctcatcacag tgcttaatat atcggaaatt    900
gagagtagat tttataaaca tccatttacc tgttttgcca agaatacaca tggtatagat    960
gcagcatata tccagttaat atatccagtc actaattcag aacgctgcga tgactgggga   1020
ctagacacca tgaggcaaat ccaagtgttt gaagatgagc cagctcgcat caagtgccca   1080
ctctttgaac acttcttgaa attcaactac agcacagccc attcagctgg ccttactctg   1140
atctggtatt ggactaggca ggaccgggac cttgaggagc caattaactt ccgcctcccc   1200
gagaaccgca ttagtaagga gaaagatgtg ctgtggttcc ggcccactct cctcaatgac   1260
actggcaact atacctgcat gttaaggaac actacatatt gcagcaaagt tgcatttccc   1320
ttggaagttg ttcaaaaaga cagctgtttc aattccccca tgaaactccc agtgcataaa   1380
ctgtatatag aatatggcat tcagaggatc acttgtccaa atgtagatgg atattttcct   1440
tccagtgtca aaccgactat cacttggtat atgggctgtt ataaaataca gaattttaat   1500
aatgtaatac ccgaaggtat gaacttgagt ttcctcattg ccttaatttc aaataatgga   1560
aattacacat gtgttgttac atatccagaa aatggacgta cgtttcatct caccaggact   1620
ctgactgtaa aggtagtagg ctctccaaaa aatgcagtgc cccctgtgat ccattcacct   1680
aatgatcatg tggtctatga gaaagaacca ggagaggagc tactcattcc ctgtacggtc   1740
tattttagtt ttctgatgga ttctcgcaat gaggtttggt ggaccattga tggaaaaaaa   1800
cctgatgaca tcactattga tgtcaccatt aacgaaagta taagtcatag tagaacagaa   1860
gatgaaacaa gaactcagat tttgagcatc aagaaagtta cctctgagga tctcaagcgc   1920
agctatgtct gtcatgctag aagtgccaaa ggcgaagttg ccaaagcagc caaggtgaag   1980
cagaaagtgc cagctccaag atacacagtg gaatccggag agtccaaata cggtccgcca   2040
tgcccatcat gcccagcacc tgagttcctg gggggaccat cagtcttcct gttcccccca   2100
aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
cagccggaga acaactacaa gaccacgcct cccgtgctgg actccgacgg ctccttcttc   2580
ctctacagca ggctaaccgt ggacaagagc aggtggcagg aggggaatgt cttctcatgc   2640
tccgtgatgc atgaggctct gcacaaccac tacacacaga agagcctctc cctgtctctg   2700
```

ggtaaatga 2709

<210> SEQ ID NO 6
<211> LENGTH: 902
<212> TYPE: PRT
<213> ORGANISM: Homo sapiens

<400> SEQUENCE: 6

```
Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
```

```
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800
```

```
Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900


<210> SEQ ID NO 7
<211> LENGTH: 2709
<212> TYPE: DNA
<213> ORGANISM: Homo sapiens

<400> SEQUENCE: 7

atggtgttac tcagacttat ttgtttcata gctctactga tttcttctct ggaggctgat      60

aaatgcaagg aacgtgaaga aaaaataatt ttagtgtcat ctgcaaatga aattgatgtt     120

cgtccctgtc ctcttaaccc aaatgaacac aaaggcacta taacttggta taaggatgac     180

agcaagacac ctgtatctac agaacaagcc tccaggattc atcaacacaa agagaaactt     240

tggtttgttc ctgctaaggt ggaggattca ggacattact attgcgtggt aagaaattca     300

tcttactgcc tcagaattaa aataagtgca aaatttgtgg agaatgagcc taacttatgt     360

tataatgcac aagccatatt taagcagaaa ctacccgttg caggagacgg aggacttgtg     420

tgcccttata tggagttttt taaaaatgaa aataatgagt tacctaaatt acagtggtat     480

aaggattgca aacctctact tcttgacaat atacacttta gtggagtcaa agataggctc     540

atcgtgatga atgtggctga aaagcataga gggaactata cttgtcatgc atcctacaca     600

tacttgggca agcaatatcc tattacccgg gtaatagaat ttattactct agaggaaaac     660

aaacccacaa ggcctgtgat tgtgagccca gctaatgaga caatggaagt agacttggga     720

tcccagatac aattgatctg taatgtcacc ggccagttga gtgacattgc ttactggaag     780

tggaatgggt cagtaattga tgaagatgac ccagtgctag gggaagacta ttacagtgtg     840

gaaaatcctg caaacaaaag aaggagtacc ctcatcacag tgcttaatat atcggaaatt     900

gagagtagat tttataaaca tccatttacc tgttttgcca agaatacaca tggtatagat     960

gcagcatata tccagttaat atatccagtc actaattcag aacgctgcga tgactgggga    1020

ctagacacca tgaggcaaat ccaagtgttt gaagatgagc cagctcgcat caagtgccca    1080

ctctttgaac acttcttgaa attcaactac agcacagccc attcagctgg ccttactctg    1140

atctggtatt ggactaggca ggaccgggac cttgaggagc caattaactt ccgcctcccc    1200

gagaaccgca ttagtaagga gaaagatgtg ctgtggttcc ggcccactct cctcaatgac    1260

actggcaact atacctgcat gttaaggaac actacatatt gcagcaaagt tgcatttccc    1320

ttggaagttg ttcaaaaaga cagctgtttc aattcccccca tgaaactccc agtgcataaa    1380

ctgtatatag aatatggcat tcagaggatc acttgtccaa atgtagatgg atattttcct    1440

tccagtgtca aaccgactat cacttggtat atgggctgtt ataaaataca gaattttaat    1500

aatgtaatac ccgaaggtat gaacttgagt ttcctcattg ccttaatttc aaataatgga    1560
```

```
aattacacat gtgttgttac atatccagaa aatggacgta cgtttcatct caccaggact   1620

ctgactgtaa aggtagtagg ctctccaaaa aatgcagtgc cccctgtgat ccattcacct   1680

aatgatcatg tggtctatga gaaagaacca ggagaggagc tactcattcc ctgtacggtc   1740

tattttagtt ttctgatgga ttctcgcaat gaggtttggt ggaccattga tggaaaaaaa   1800

cctgatgaca tcactattga tgtcaccatt aacgaaagta taagtcatag tagaacagaa   1860

gatgaaacaa gaactcagat tttgagcatc aagaaagtta cctctgagga tctcaagcgc   1920

agctatgtct gtcatgctag aagtgccaaa ggcgaagttg ccaaagcagc caaggtgaag   1980

cagaaagtgc cagctccaag atacacagtg gaatccggag agtccaaata cggtccgcca   2040

tgcccaccat gcccagcacc tgagttcctg gggggaccat cagtcttcct gttcccccca   2100

aaacccaagg acactctcat gatctcccgg acccctgagg tcacgtgcgt ggtggtggac   2160

gtgagccagg aagaccccga ggtccagttc aactggtacg tggatggcgt ggaggtgcat   2220

aatgccaaga caaagccgcg ggaggagcag ttcaacagca cgtaccgtgt ggtcagcgtc   2280

ctcaccgtcc tgcaccagga ctggctgaac ggcaaggagt acaagtgcaa ggtctccaac   2340

aaaggcctcc cgtcctccat cgagaaaacc atctccaaag ccaaagggca gccccgagag   2400

ccacaggtgt acaccctgcc cccatcccag gaggagatga ccaagaacca ggtcagcctg   2460

acctgcctgg tcaaaggctt ctaccccagc gacatcgccg tggagtggga gagcaatggg   2520

cagccggaga acaactacaa gaccacgcct cccgtgctgg actccgacgg ctccttcttc   2580

ctctacagca ggctaaccgt ggacaagagc aggtggcagg aggggaatgt cttctcatgc   2640

tccgtgatgc atgaggctct gcacaaccac tacacacaga agagcctctc cctgtctctg   2700

ggtaaatga                                                           2709
```

```
<210> SEQ ID NO 8
<211> LENGTH: 902
<212> TYPE: PRT
<213> ORGANISM: Homo sapiens

<400> SEQUENCE: 8

Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
```

```
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590
```

```
Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Pro Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900
```

<210> SEQ ID NO 9
<211> LENGTH: 2703
<212> TYPE: DNA
<213> ORGANISM: Homo sapiens

<400> SEQUENCE: 9

```
atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360
```

-continued

```
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtggaaaaa   1080
tgcaaggaac gtgaagaaaa aataatttta gtgagctcag caaatgaaat cgatgttcgt   1140
ccctgtcctc ttaacccaaa tgaacacaaa ggcactataa cttggtataa ggatgacagc   1200
aagacacctg tatctacaga acaagcctcc aggattcatc aacacaaaga gaaactttgg   1260
tttgttcctg ctaaggtgga ggattcagga cattactatt gcgtggtaag aaattcatct   1320
tactgcctca gaattaaaat aagtgcaaaa tttgtggaga atgagcctaa cttatgttat   1380
aatgcacaag ccatatttaa gcagaaacta cccgttgcag gagacggagg acttgtgtgc   1440
ccttatatgg agtttttaa aaatgaaaat aatgagttac ctaaattaca gtggtataag   1500
gattgcaaac ctctacttct tgacaatata cactttagtg gagtcaaaga taggctcatc   1560
gtgatgaatg tggctgaaaa gcatagaggg aactatactt gtcatgcatc ctacacatac   1620
ttgggcaagc aatatcctat tacccgggta atagaattta ttactctaga ggaaaacaaa   1680
cccacaaggc ctgtgattgt gagcccagct aatgagacaa tggaagtaga cttgggatcc   1740
cagatacaat tgatctgtaa tgtcaccggc cagttgagtg acattgctta ctggaagtgg   1800
aatgggtcag taattgatga agatgaccca gtgctagggg aagactatta cagtgtggaa   1860
aatcctgcaa acaaaagaag gagtaccctc atcacagtgc ttaatatatc ggaaattgag   1920
agtagatttt ataaacatcc atttacctgt tttgccaaga atacacatgg tatagatgca   1980
gcatatatcc agttaatata tccagtcact aattccggag acaaaactca cacatgccca   2040
ccgtgcccag cacctgaact cctgggggga ccgtcagtct tcctcttccc cccaaaaccc   2100
aaggacaccc tcatgatctc ccggacccct gaggtcacat gcgtggtggt ggacgtgagc   2160
cacgaagacc ctgaggtcaa gttcaactgg tacgtggacg gcgtggaggt gcataatgcc   2220
aagacaaagc cgcgggagga gcagtacaac agcacgtacc gtgtggtcag cgtcctcacc   2280
gtcctgcacc aggactggct gaatggcaag gagtacaagt gcaaggtctc caacaaagcc   2340
ctcccagccc ccatcgagaa aaccatctcc aaagccaaag ggcagccccg agaaccacag   2400
gtgtacaccc tgcccccatc ccgggatgag ctgaccaaga accaggtcag cctgacctgc   2460
ctggtcaaag gcttctatcc cagcgacatc gccgtggagt gggagagcaa tgggcagccg   2520
gagaacaact acaagaccac gcctcccgtg ctggactccg acggctcctt cttcctctac   2580
agcaagctca ccgtggacaa gagcaggtgg cagcagggga acgtcttctc atgctccgtg   2640
atgcatgagg ctctgcacaa ccactacacg cagaagagcc tctccctgtc tccgggtaaa   2700
tga                                                                 2703
```

```
<210> SEQ ID NO 10
<211> LENGTH: 900
<212> TYPE: PRT
<213> ORGANISM: Homo sapiens

<400> SEQUENCE: 10

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380
```

```
Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Asp Lys Thr His Thr Cys Pro Pro Cys Pro Ala Pro Glu Leu Leu
        675                 680                 685

Gly Gly Pro Ser Val Phe Leu Phe Pro Pro Lys Pro Lys Asp Thr Leu
    690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
        755                 760                 765

Gly Lys Glu Tyr Lys Cys Lys Val Ser Asn Lys Ala Leu Pro Ala Pro
    770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                805                 810                 815
```

```
Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900


<210> SEQ ID NO 11
<211> LENGTH: 2709
<212> TYPE: DNA
<213> ORGANISM: Homo sapiens

<400> SEQUENCE: 11

atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360

tattgcagca aagttgcatt tcccttggaa gttgttcaaa aagacagctg tttcaattcc     420

cccatgaaac tcccagtgca taaactgtat atagaatatg gcattcagag gatcacttgt     480

ccaaatgtag atggatattt tccttccagt gtcaaaccga ctatcacttg gtatatgggc     540

tgttataaaa tacagaattt taataatgta atacccgaag gtatgaactt gagtttcctc     600

attgccttaa tttcaaataa tggaaattac acatgtgttg ttacatatcc agaaaatgga     660

cgtacgtttc atctcaccag gactctgact gtaaaggtag taggctctcc aaaaaatgca     720

gtgccccctg tgatccattc acctaatgat catgtggtct atgagaaaga accaggagag     780

gagctactca ttccctgtac ggtctatttt agttttctga tggattctcg caatgaggtt     840

tggtggacca ttgatggaaa aaaacctgat gacatcacta ttgatgtcac cattaacgaa     900

agtataagtc atagtagaac agaagatgaa acaagaactc agattttgag catcaagaaa     960

gttacctctg aggatctcaa gcgcagctat gtctgtcatg ctagaagtgc caaaggcgaa    1020

gttgccaaag cagccaaggt gaagcagaaa gtgccagctc caagatacac agtggaaaaa    1080

tgcaaggaac gtgaagaaaa aataatttta gtgagctcag caaatgaaat cgatgttcgt    1140

ccctgtcctc ttaacccaaa tgaacacaaa ggcactataa cttggtataa ggatgacagc    1200

aagacacctg tatctacaga acaagcctcc aggattcatc aacacaaaga gaaactttgg    1260

tttgttcctg ctaaggtgga ggattcagga cattactatt gcgtggtaag aaattcatct    1320

tactgcctca gaattaaaat aagtgcaaaa tttgtggaga atgagcctaa cttatgttat    1380

aatgcacaag ccatatttaa gcagaaacta cccgttgcag gagacggagg acttgtgtgc    1440

ccttatatgg agtttttaa aaatgaaaat aatgagttac ctaaattaca gtggtataag     1500

gattgcaaac ctctacttct tgacaatata cactttagtg gagtcaaaga taggctcatc    1560

gtgatgaatg tggctgaaaa gcatagaggg aactatactt gtcatgcatc ctacacatac    1620
```

```
ttgggcaagc aatatcctat tacccgggta atagaattta ttactctaga ggaaaacaaa   1680

cccacaaggc ctgtgattgt gagcccagct aatgagacaa tggaagtaga cttgggatcc   1740

cagatacaat tgatctgtaa tgtcaccggc cagttgagtg acattgctta ctggaagtgg   1800

aatgggtcag taattgatga agatgaccca gtgctagggg aagactatta cagtgtggaa   1860

aatcctgcaa acaaaagaag gagtaccctc atcacagtgc ttaatatatc ggaaattgag   1920

agtagatttt ataaacatcc atttacctgt tttgccaaga atacacatgg tatagatgca   1980

gcatatatcc agttaatata tccagtcact aattccggag agtccaaata cggtccgcca   2040

tgcccatcat gcccagcacc tgagttcctg gggggaccat cagtcttcct gttcccccca   2100

aaacccaagg acactctcat gatctcccgg acccctgagg tcacgtgcgt ggtggtggac   2160

gtgagccagg aagaccccga ggtccagttc aactggtacg tggatggcgt ggaggtgcat   2220

aatgccaaga caaagccgcg ggaggagcag ttcaacagca cgtaccgtgt ggtcagcgtc   2280

ctcaccgtcc tgcaccagga ctggctgaac ggcaaggagt acaagtgcaa ggtctccaac   2340

aaaggcctcc cgtcctccat cgagaaaacc atctccaaag ccaaagggca gccccgagag   2400

ccacaggtgt acaccctgcc cccatcccag gaggagatga ccaagaacca ggtcagcctg   2460

acctgcctgg tcaaaggctt ctaccccagc gacatcgccg tggagtggga gagcaatggg   2520

cagccggaga acaactacaa gaccacgcct cccgtgctgg actccgacgg ctccttcttc   2580

ctctacagca ggctaaccgt ggacaagagc aggtggcagg aggggaatgt cttctcatgc   2640

tccgtgatgc atgaggctct gcacaaccac tacacacaga agagcctctc cctgtctctg   2700

ggtaaatga                                                           2709
```

<210> SEQ ID NO 12
<211> LENGTH: 902
<212> TYPE: PRT
<213> ORGANISM: Homo sapiens

<400> SEQUENCE: 12

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175
```

```
Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605
```

```
Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900
```

<210> SEQ ID NO 13
<211> LENGTH: 2709
<212> TYPE: DNA
<213> ORGANISM: Homo sapiens

<400> SEQUENCE: 13

```
atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360

tattgcagca aagttgcatt tcccttggaa gttgttcaaa aagacagctg tttcaattcc     420
```

```
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtggaaaaa   1080
tgcaaggaac gtgaagaaaa aataatttta gtgagctcag caaatgaaat cgatgttcgt   1140
ccctgtcctc ttaacccaaa tgaacacaaa ggcactataa cttggtataa ggatgacagc   1200
aagacacctg tatctacaga acaagcctcc aggattcatc aacacaaaga gaaactttgg   1260
tttgttcctg ctaaggtgga ggattcagga cattactatt gcgtggtaag aaattcatct   1320
tactgcctca gaattaaaat aagtgcaaaa tttgtggaga atgagcctaa cttatgttat   1380
aatgcacaag ccatatttaa gcagaaacta cccgttgcag gagacggagg acttgtgtgc   1440
ccttatatgg agttttttaa aaatgaaaat aatgagttac ctaaattaca gtggtataag   1500
gattgcaaac ctctacttct tgacaatata cactttagtg gagtcaaaga taggctcatc   1560
gtgatgaatg tggctgaaaa gcatagaggg aactatactt gtcatgcatc ctacacatac   1620
ttgggcaagc aatatcctat tacccgggta atagaattta ttactctaga ggaaaacaaa   1680
cccacaaggc ctgtgattgt gagcccagct aatgagacaa tggaagtaga cttgggatcc   1740
cagatacaat tgatctgtaa tgtcaccggc cagttgagtg acattgctta ctggaagtgg   1800
aatgggtcag taattgatga agatgaccca gtgctagggg aagactatta cagtgtggaa   1860
aatcctgcaa acaaaagaag gagtaccctc atcacagtgc ttaatatatc ggaaattgag   1920
agtagatttt ataaacatcc atttacctgt tttgccaaga atacacatgg tatagatgca   1980
gcatatatcc agttaatata tccagtcact aattccggag agtccaaata cggtccgcca   2040
tgcccaccat gcccagcacc tgagttcctg gggggaccat cagtcttcct gttcccccca   2100
aaacccaagg acactctcat gatctcccgg acccctgagg tcacgtgcgt ggtggtggac   2160
gtgagccagg aagaccccga ggtccagttc aactggtacg tggatggcgt ggaggtgcat   2220
aatgccaaga caaagccgcg ggaggagcag ttcaacagca cgtaccgtgt ggtcagcgtc   2280
ctcaccgtcc tgcaccagga ctggctgaac ggcaaggagt acaagtgcaa ggtctccaac   2340
aaaggcctcc cgtcctccat cgagaaaacc atctccaaag ccaaagggca gccccgagag   2400
ccacaggtgt acaccctgcc cccatcccag gaggagatga ccaagaacca ggtcagcctg   2460
acctgcctgg tcaaaggctt ctaccccagc gacatcgccg tggagtggga gagcaatggg   2520
cagccggaga acaactacaa gaccacgcct cccgtgctgg actccgacgg ctccttcttc   2580
ctctacagca ggctaaccgt ggacaagagc aggtggcagg aggggaatgt cttctcatgc   2640
tccgtgatgc atgaggctct gcacaaccac tacacacaga agagcctctc cctgtctctg   2700
ggtaaatga                                                           2709
```

<210> SEQ ID NO 14

<211> LENGTH: 902
<212> TYPE: PRT
<213> ORGANISM: Homo sapiens

<400> SEQUENCE: 14

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400
```

```
Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Glu Ser Lys Tyr Gly Pro Pro Cys Pro Pro Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
```

```
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900


<210> SEQ ID NO 15
<211> LENGTH: 2748
<212> TYPE: DNA
<213> ORGANISM: Homo sapiens

<400> SEQUENCE: 15

atggtgcgct tgtacgtgtt ggtaatggga gtttctgcct tcacccttca gcctgcggca      60

cacacagggg ctgccagaag ctgccggttt cgtgggaggc attacaagcg ggagttcagg     120

ctggaagggg agcctgtagc cctgaggtgc ccccaggtgc cctactggtt gtgggcctct     180

gtcagccccc gcatcaacct gacatggcat aaaaatgact ctgctaggac ggtcccagga     240

gaagaagaga cacggatgtg ggcccaggac ggtgctctgt ggcttctgcc agccttgcag     300

gaggactctg gcacctacgt ctgcactact agaaatgctt cttactgtga caaaatgtcc     360

attgagctca gagtttttga gaatacagat gctttcctgc cgttcatctc atacccgcaa     420

attttaacct tgtcaacctc tggggtatta gtatgccctg acctgagtga attcacccgt     480

gacaaaactg acgtgaagat tcaatggtac aaggattctc ttcttttgga taaagacaat     540

gagaaatttc taagtgtgag gggaccact cacttactcg tacacgatgt ggccctggaa      600

gatgctggct attaccgctg tgtcctgaca tttgcccatg aaggccagca atacaacatc     660

actaggagta ttgagctacg catcaagaaa aaaaaagaag agaccattcc tgtgatcatt     720

tccccccctca agaccatatc agcttctctg ggtcaagac tgacaatccc atgtaaggtg     780

tttctgggaa ccggcacacc cttaaccacc atgctgtggt ggacggccaa tgacacccac     840

atagagagcg cctacccggg aggccgcgtg accgaggggc cacgccagga atattcagaa     900

aataatgaga actacattga agtgccattg atttttgatc ctgtcacaag agaggatttg     960

cacatggatt ttaaatgtgt tgtccataat accctgagtt ttcagacact acgcaccaca    1020

gtcaaggaag cctcctccac gttctcagaa cgctgcgatg actggggact agacaccatg    1080

aggcaaatcc aagtgtttga agatgagcca gctcgcatca agtgcccact ctttgaacac    1140

ttcttgaaat tcaactacag cacagcccat tcagctggcc ttactctgat ctggtattgg    1200

actaggcagg accgggacct tgaggagcca attaacttcc gcctccccga gaaccgcatt    1260

agtaaggaga aagatgtgct gtggttccgg cccactctcc tcaatgacac tggcaactat    1320

acctgcatgt taaggaacac tacatattgc agcaaagttg catttccctt ggaagttgtt    1380

caaaaagaca gctgtttcaa ttcccccatg aaactcccag tgcataaact gtatatagaa    1440

tatggcattc agaggatcac ttgtccaaat gtagatggat attttccttc cagtgtcaaa    1500

ccgactatca cttggtatat gggctgttat aaaatacaga attttaataa tgtaataccc    1560

gaaggtatga acttgagttt cctcattgcc ttaatttcaa ataatggaaa ttacacatgt    1620

gttgttacat atccagaaaa tggacgtacg tttcatctca ccaggactct gactgtaaag    1680
```

```
gtagtaggct ctccaaaaaa tgcagtgccc cctgtgatcc attcacctaa tgatcatgtg   1740

gtctatgaga aagaaccagg agaggagcta ctcattccct gtacggtcta ttttagtttt   1800

ctgatggatt ctcgcaatga ggtttggtgg accattgatg gaaaaaaacc tgatgacatc   1860

actattgatg tcaccattaa cgaaagtata agtcatagta gaacagaaga tgaaacaaga   1920

actcagattt tgagcatcaa gaaagttacc tctgaggatc tcaagcgcag ctatgtctgt   1980

catgctagaa gtgccaaagg cgaagttgcc aaagcagcca aggtgaagca gaaagtgcca   2040

gctccaagat acacagtgtc cggagacaaa actcacacat gcccaccgtg cccagcacct   2100

gaactcctgg ggggaccgtc agtcttcctc ttccccccaa aacccaagga caccctcatg   2160

atctcccgga cccctgaggt cacatgcgtg gtggtggacg tgagccacga agaccctgag   2220

gtcaagttca actggtacgt ggacggcgtg gaggtgcata atgccaagac aaagccgcgg   2280

gaggagcagt acaacagcac gtaccgtgtg gtcagcgtcc tcaccgtcct gcaccaggac   2340

tggctgaatg gcaaggagta caagtgcaag gtctccaaca aagccctccc agcccccatc   2400

gagaaaacca tctccaaagc caaagggcag ccccgagaac cacaggtgta caccctgccc   2460

ccatcccggg atgagctgac caagaaccag gtcagcctga cctgcctggt caaaggcttc   2520

tatcccagcg acatcgccgt ggagtgggag agcaatgggc agccggagaa caactacaag   2580

accacgcctc ccgtgctgga ctccgacggc tccttcttcc tctatagcaa gctcaccgtg   2640

gacaagagca ggtggcagca ggggaacgtc ttctcatgct ccgtgatgca tgaggctctg   2700

cacaaccact acacgcagaa gagcctctcc ctgtctccgg gtaaatga                2748
```

<210> SEQ ID NO 16
<211> LENGTH: 915
<212> TYPE: PRT
<213> ORGANISM: Homo sapiens

<400> SEQUENCE: 16

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190
```

```
Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
```

```
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
915


<210> SEQ ID NO 17
<211> LENGTH: 2754
<212> TYPE: DNA
<213> ORGANISM: Homo sapiens

<400> SEQUENCE: 17

atggtgcgct tgtacgtgtt ggtaatggga gtttctgcct tcacccttca gcctgcggca     60

cacacagggg ctgccagaag ctgccggttt cgtgggaggc attacaagcg ggagttcagg    120

ctggaagggg agcctgtagc cctgaggtgc ccccaggtgc cctactggtt gtgggcctct    180

gtcagccccc gcatcaacct gacatggcat aaaaatgact ctgctaggac ggtcccagga    240

gaagaagaga cacggatgtg ggcccaggac ggtgctctgt ggcttctgcc agccttgcag    300

gaggactctg gcacctacgt ctgcactact agaaatgctt cttactgtga caaaatgtcc    360

attgagctca gagtttttga gaatacagat gctttcctgc cgttcatctc ataccegcaa    420
```

-continued

```
attttaacct tgtcaacctc tggggtatta gtatgccctg acctgagtga attcacccgt    480
gacaaaactg acgtgaagat tcaatggtac aaggattctc ttcttttgga taaagacaat    540
gagaaatttc taagtgtgag gggaccact cacttactcg tacacgatgt ggccctggaa    600
gatgctggct attaccgctg tgtcctgaca tttgcccatg aaggccagca atacaacatc    660
actaggagta ttgagctacg catcaagaaa aaaaaagaag agaccattcc tgtgatcatt    720
tccccctca agaccatatc agcttctctg ggtcaagac tgacaatccc atgtaaggtg    780
tttctgggaa ccggcacacc cttaaccacc atgctgtggt ggacggccaa tgacacccac    840
atagagagcg cctacccggg aggccgcgtg accgaggggc cacgccagga atattcagaa    900
aataatgaga actacattga agtgccattg atttttgatc ctgtcacaag agaggatttg    960
cacatggatt ttaaatgtgt tgtccataat accctgagtt ttcagacact acgcaccaca   1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctccccga gaaccgcatt   1260
agtaaggaga aagatgtgct gtggttccgg cccactctcc tcaatgacac tggcaactat   1320
acctgcatgt taaggaacac tacatattgc agcaaagttg catttccctt ggaagttgtt   1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga attttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg gaaaaaaacc tgatgacatc   1860
actattgatg tcaccattaa cgaaagtata agtcatagta gaacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagagtcc aaatacggtc cgccatgccc atcatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgcccccat cccaggagga gatgaccaag aaccaggtca gcctgacctg cctggtcaaa   2520
ggcttctacc ccagcgacat cgccgtggag tgggagagca atgggcagcc ggagaacaac   2580
tacaagacca cgcctcccgt gctggactcc gacggctcct tcttcctcta cagcaggcta   2640
accgtggaca agagcaggtg gcaggagggg aatgtcttct catgctccgt gatgcatgag   2700
gctctgcaca accactacac acagaagagc ctctccctgt ctctgggtaa atga         2754
```

<210> SEQ ID NO 18
<211> LENGTH: 917
<212> TYPE: PRT
<213> ORGANISM: Homo sapiens

<400> SEQUENCE: 18

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
```

```
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Glu Ser Lys Tyr Gly Pro Pro Cys Pro Ser Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815
```

```
Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915


<210> SEQ ID NO 19
<211> LENGTH: 2754
<212> TYPE: DNA
<213> ORGANISM: Homo sapiens

<400> SEQUENCE: 19

atggtgcgct tgtacgtgtt ggtaatggga gtttctgcct tcacccttca gcctgcggca      60

cacacagggg ctgccagaag ctgccggttt cgtgggaggc attacaagcg ggagttcagg     120

ctggaagggg agcctgtagc cctgaggtgc ccccaggtgc cctactggtt gtgggcctct     180

gtcagccccc gcatcaacct gacatggcat aaaaatgact ctgctaggac ggtcccagga     240

gaagaagaga cacggatgtg ggcccaggac ggtgctctgt ggcttctgcc agccttgcag     300

gaggactctg gcacctacgt ctgcactact agaaatgctt cttactgtga caaaatgtcc     360

attgagctca gagtttttga gaatacagat gctttcctgc cgttcatctc atacccgcaa     420

attttaacct tgtcaacctc tggggtatta gtatgccctg acctgagtga attcacccgt     480

gacaaaactg acgtgaagat tcaatggtac aaggattctc ttcttttgga taaagacaat     540

gagaaatttc taagtgtgag gggaccact cacttactcg tacacgatgt ggccctggaa     600

gatgctggct attaccgctg tgtcctgaca tttgcccatg aaggccagca atacaacatc     660

actaggagta ttgagctacg catcaagaaa aaaaaagaag agaccattcc tgtgatcatt     720

tccccctca agaccatatc agcttctctg gggtcaagac tgacaatccc atgtaaggtg     780

tttctgggaa ccggcacacc cttaaccacc atgctgtggt ggacggccaa tgacacccac     840

atagagagcg cctacccggg aggccgcgtg accgaggggc cacgccagga atattcagaa     900

aataatgaga actacattga agtgccattg atttttgatc ctgtcacaag agaggatttg     960

cacatggatt ttaaatgtgt tgtccataat accctgagtt ttcagacact acgcaccaca    1020

gtcaaggaag cctcctccac gttctcagaa cgctgcgatg actggggact agacaccatg    1080

aggcaaatcc aagtgtttga agatgagcca gctcgcatca agtgcccact ctttgaacac    1140

ttcttgaaat tcaactacag cacagcccat tcagctggcc ttactctgat ctggtattgg    1200

actaggcagg accgggacct tgaggagcca attaacttcc gcctccccga gaaccgcatt    1260

agtaaggaga aagatgtgct gtggttccgg cccactctcc tcaatgacac tggcaactat    1320

acctgcatgt taaggaacac tacatattgc agcaaagttg catttccctt ggaagttgtt    1380

caaaaagaca gctgtttcaa ttcccccatg aaactcccag tgcataaact gtatatagaa    1440

tatggcattc agaggatcac ttgtccaaat gtagatggat attttccttc cagtgtcaaa    1500

ccgactatca cttggtatat gggctgttat aaaatacaga atttaataa tgtaataccc    1560
```

```
gaaggtatga acttgagttt cctcattgcc ttaatttcaa ataatggaaa ttacacatgt   1620

gttgttacat atccagaaaa tggacgtacg tttcatctca ccaggactct gactgtaaag   1680

gtagtaggct ctccaaaaaa tgcagtgccc cctgtgatcc attcacctaa tgatcatgtg   1740

gtctatgaga aagaaccagg agaggagcta ctcattccct gtacggtcta ttttagtttt   1800

ctgatggatt ctcgcaatga ggtttggtgg accattgatg gaaaaaaacc tgatgacatc   1860

actattgatg tcaccattaa cgaaagtata agtcatagta gaacagaaga tgaaacaaga   1920

actcagattt tgagcatcaa gaaagttacc tctgaggatc tcaagcgcag ctatgtctgt   1980

catgctagaa gtgccaaagg cgaagttgcc aaagcagcca aggtgaagca gaaagtgcca   2040

gctccaagat acacagtgtc cggagagtcc aaatacggtc cgccatgccc accatgccca   2100

gcacctgagt tcctgggggg accatcagtc ttcctgttcc ccccaaaacc caaggacact   2160

ctcatgatct cccggacccc tgaggtcacg tgcgtggtgg tggacgtgag ccaggaagac   2220

cccgaggtcc agttcaactg gtacgtggat ggcgtggagg tgcataatgc caagacaaag   2280

ccgcgggagg agcagttcaa cagcacgtac cgtgtggtca gcgtcctcac cgtcctgcac   2340

caggactggc tgaacggcaa ggagtacaag tgcaaggtct ccaacaaagg cctcccgtcc   2400

tccatcgaga aaaccatctc caaagccaaa gggcagcccc gagagccaca ggtgtacacc   2460

ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754
```

<210> SEQ ID NO 20
<211> LENGTH: 917
<212> TYPE: PRT
<213> ORGANISM: Homo sapiens

<400> SEQUENCE: 20

```
Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
```

```
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590
```

```
Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915


<210> SEQ ID NO 21
<211> LENGTH: 2748
<212> TYPE: DNA
<213> ORGANISM: Homo sapiens

<400> SEQUENCE: 21

atggtgcttc tgtggtgtgt agtgagtctc tacttttatg gaatcctgca aagtgatgcc      60

tcagaacgct gcgatgactg ggactagac accatgaggc aaatccaagt gtttgaagat      120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300
```

-continued

```
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtgcacaca   1080
ggggctgcca gaagctgccg gtttcgtggg aggcattaca agcgggagtt caggctggaa   1140
ggggagcctg tagccctgag gtgcccccag gtgccctact ggttgtgggc ctctgtcagc   1200
ccccgcatca acctgacatg gcataaaaat gactctgcta ggacggtccc aggagaagaa   1260
gagacacgga tgtgggccca ggacggtgct ctgtggcttc tgccagcctt gcaggaggac   1320
tctggcacct acgtctgcac tactagaaat gcttcttact gtgacaaaat gtccattgag   1380
ctcagagttt ttgagaatac agatgctttc ctgccgttca tctcataccc gcaaatttta   1440
accttgtcaa cctctggggt attagtatgc cctgacctga gtgaattcac ccgtgacaaa   1500
actgacgtga agattcaatg gtacaaggat tctcttcttt tggataaaga caatgagaaa   1560
tttctaagtg tgagggggac cactcactta ctcgtacacg atgtggccct ggaagatgct   1620
ggctattacc gctgtgtcct gacatttgcc catgaaggcc agcaatacaa catcactagg   1680
agtattgagc tacgcatcaa gaaaaaaaaa gaagagacca ttcctgtgat catttccccc   1740
ctcaagacca tatcagcttc tctggggtca agactgacaa tcccatgtaa ggtgtttctg   1800
ggaaccggca caccccttaac caccatgctg tggtggacgg ccaatgacac ccacatagag   1860
agcgcctacc cgggaggccg cgtgaccgag gggccacgcc aggaatattc agaaaataat   1920
gagaactaca ttgaagtgcc attgattttt gatcctgtca caagagagga tttgcacatg   1980
gattttaaat gtgttgtcca taataccctg agttttcaga cactacgcac cacagtcaag   2040
gaagcctcct ccacgttctc cggagacaaa actcacacat gcccaccgtg cccagcacct   2100
gaactcctgg ggggaccgtc agtcttcctc ttccccccaa aacccaagga caccctcatg   2160
atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caaagggcag ccccgagaac cacaggtgta caccctgccc   2460
ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctatagcaa gctcaccgtg   2640
gacaagagca ggtggcagca ggggaacgtc ttctcatgct ccgtgatgca tgaggctctg   2700
```

```
cacaaccact acacgcagaa gagcctctcc ctgtctccgg gtaaatga              2748


<210> SEQ ID NO 22
<211> LENGTH: 915
<212> TYPE: PRT
<213> ORGANISM: Homo sapiens

<400> SEQUENCE: 22

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365
```

```
Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800
```

```
Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915
```

<210> SEQ ID NO 23
<211> LENGTH: 2754
<212> TYPE: DNA
<213> ORGANISM: Homo sapiens

<400> SEQUENCE: 23

```
atggtgcttc tgtggtgtgt agtgagtctc tacttttatg gaatcctgca aagtgatgcc      60

tcagaacgct gcgatgactg ggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360

tattgcagca aagttgcatt tcccttggaa gttgttcaaa aagacagctg tttcaattcc     420

cccatgaaac tcccagtgca taaactgtat atagaatatg gcattcagag gatcacttgt     480

ccaaatgtag atggatattt tccttccagt gtcaaaccga ctatcacttg gtatatgggc     540

tgttataaaa tacagaattt taataatgta atacccgaag gtatgaactt gagtttcctc     600

attgccttaa tttcaaataa tggaaattac acatgtgttg ttacatatcc agaaaatgga     660

cgtacgtttc atctcaccag gactctgact gtaaaggtag taggctctcc aaaaaatgca     720

gtgcccccctg tgatccattc acctaatgat catgtggtct atgagaaaga accaggagag     780

gagctactca ttccctgtac ggtctatttt agtttttctga tggattctcg caatgaggtt     840

tggtggacca ttgatggaaa aaaacctgat gacatcacta ttgatgtcac cattaacgaa     900

agtataagtc atagtagaac agaagatgaa acaagaactc agattttgag catcaagaaa     960

gttacctctg aggatctcaa gcgcagctat gtctgtcatg ctagaagtgc caaaggcgaa    1020

gttgccaaag cagccaaggt gaagcagaaa gtgccagctc caagatacac agtgcacaca    1080

ggggctgcca gaagctgccg gtttcgtggg aggcattaca agcgggagtt caggctggaa    1140

ggggagcctg tagccctgag gtgcccccag gtgccctact ggttgtgggc ctctgtcagc    1200

ccccgcatca acctgacatg gcataaaaat gactctgcta ggacggtccc aggagaagaa    1260

gagacacgga tgtgggccca ggacggtgct ctgtggcttc tgccagcctt gcaggaggac    1320

tctggcacct acgtctgcac tactagaaat gcttcttact gtgacaaaat gtccattgag    1380

ctcagagttt ttgagaatac agatgctttc ctgccgttca tctcataccc gcaaatttta    1440
```

```
accttgtcaa cctctggggt attagtatgc cctgacctga gtgaattcac ccgtgacaaa   1500

actgacgtga agattcaatg gtacaaggat tctcttcttt tggataaaga caatgagaaa   1560

tttctaagtg tgagggggac cactcactta ctcgtacacg atgtggccct ggaagatgct   1620

ggctattacc gctgtgtcct gacatttgcc catgaaggcc agcaatacaa catcactagg   1680

agtattgagc tacgcatcaa gaaaaaaaaa gaagagacca ttcctgtgat catttccccc   1740

ctcaagacca tatcagcttc tctggggtca agactgacaa tcccatgtaa ggtgtttctg   1800

ggaaccggca cacccttaac caccatgctg tggtggacgg ccaatgacac ccacatagag   1860

agcgcctacc cgggaggccg cgtgaccgag gggccacgcc aggaatattc agaaaataat   1920

gagaactaca ttgaagtgcc attgattttt gatcctgtca caagagagga tttgcacatg   1980

gattttaaat gtgttgtcca taataccctg agttttcaga cactacgcac cacagtcaag   2040

gaagcctcct ccacgttctc cggagagtcc aaatacggtc cgccatgccc atcatgccca   2100

gcacctgagt tcctgggggg accatcagtc ttcctgttcc ccccaaaacc caaggacact   2160

ctcatgatct cccggacccc tgaggtcacg tgcgtggtgg tggacgtgag ccaggaagac   2220

cccgaggtcc agttcaactg gtacgtggat ggcgtggagg tgcataatgc caagacaaag   2280

ccgcgggagg agcagttcaa cagcacgtac cgtgtggtca gcgtcctcac cgtcctgcac   2340

caggactggc tgaacggcaa ggagtacaag tgcaaggtct ccaacaaagg cctcccgtcc   2400

tccatcgaga aaaccatctc caaagccaaa gggcagcccc gagagccaca ggtgtacacc   2460

ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754
```

<210> SEQ ID NO 24
<211> LENGTH: 917
<212> TYPE: PRT
<213> ORGANISM: Homo sapiens

<400> SEQUENCE: 24

```
Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140
```

```
Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575
```

```
Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Ser Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915

<210> SEQ ID NO 25
<211> LENGTH: 2754
<212> TYPE: DNA
<213> ORGANISM: Homo sapiens

<400> SEQUENCE: 25

atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180
```

```
gcccattcag ctggccttac tctgatctgg tattggacta ggcaggaccg ggaccttgag    240
gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgcccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtgcacaca   1080
ggggctgcca gaagctgccg gtttcgtggg aggcattaca agcgggagtt caggctggaa   1140
ggggagcctg tagccctgag gtgcccccag gtgccctact ggttgtgggc ctctgtcagc   1200
cccccgcatca acctgacatg gcataaaaat gactctgcta ggacggtccc aggagaagaa   1260
gagacacgga tgtgggccca ggacggtgct ctgtggcttc tgccagcctt gcaggaggac   1320
tctggcacct acgtctgcac tactagaaat gcttcttact gtgacaaaat gtccattgag   1380
ctcagagttt ttgagaatac agatgctttc ctgccgttca tctcataccc gcaaatttta   1440
accttgtcaa cctctggggt attagtatgc cctgacctga gtgaattcac ccgtgacaaa   1500
actgacgtga agattcaatg gtacaaggat tctcttcttt tggataaaga caatgagaaa   1560
tttctaagtg tgaggggggac cactcactta ctcgtacacg atgtggccct ggaagatgct   1620
ggctattacc gctgtgtcct gacatttgcc catgaaggcc agcaatacaa catcactagg   1680
agtattgagc tacgcatcaa gaaaaaaaaa gaagagacca ttcctgtgat catttccccc   1740
ctcaagacca tatcagcttc tctggggtca agactgacaa tcccatgtaa ggtgtttctg   1800
ggaaccggca cacccttaac caccatgctg tggtggacgg ccaatgacac ccacatagag   1860
agcgcctacc cgggaggccg cgtgaccgag ggccacgcc aggaatattc agaaaataat   1920
gagaactaca ttgaagtgcc attgattttt gatcctgtca caagagagga tttgcacatg   1980
gattttaaat gtgttgtcca taataccctg agttttcaga cactacgcac cacagtcaag   2040
gaagcctcct ccacgttctc cggagagtcc aaatacggtc cgccatgccc accatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgcccccat cccaggagga gatgaccaag aaccaggtca gcctgacctg cctggtcaaa   2520
ggcttctacc ccagcgacat cgccgtggag tgggagagca atgggcagcc ggagaacaac   2580
```

```
tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga          2754


<210> SEQ ID NO 26
<211> LENGTH: 917
<212> TYPE: PRT
<213> ORGANISM: Homo sapiens

<400> SEQUENCE: 26

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350
```

```
Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
```

```
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915
```

USE OF IL-1 ANTAGONISTS TO TREAT GOUT

CROSS-REFERENCE TO RELATED APPLICATIONS

This application is a continuation of U.S. patent application Ser. No. 12/567,816, filed on Sep. 28, 2009, now U.S. Pat. No. 7,820,154, which is a continuation of U.S. patent application Ser. No. 12/200,681, filed on Aug. 28, 2008, now U.S. Pat. No. 7,632,490, which is a continuation-in-part of U.S. patent application Ser. No. 11/975,593 filed on Oct. 19, 2007, now abandoned, which claims the benefit under 35 USC §119(e) of U.S. Provisional 60/853,385 filed on Oct. 20, 2006, which applications are herein specifically incorporated by reference in their entireties.

BACKGROUND

1. Field of the Invention

The invention relates to methods of using interleukin-1 (IL-1) antagonists to treat metabolic rheumatic disorders associated with hyperuricemia, including gout, and chronic active (refractory) gout. Further, the invention encompasses treatment of conditions such as pseudogout and drug-induced gout.

2. Description of Related Art

Metabolic rheumatic disorders associated with hyperuricemia, such as gout, are characterized by perversion of the purine metabolism resulting in hyperuricemia, i.e. an excess of uric acid in the blood, attacks of acute arthritis, and formation of chalky deposits in the cartilages of the joints. These deposits are made up chiefly of urates, or uric acid.

Known methods for treating gout include the use of uric acid synthesis inhibitors to inhibit the accumulation of uric acid in the body, and use of uric acid excretion promoters to accelerate the rapid excretion of uric acid accumulated in the body. Allopurinol is an example of a uric acid synthesis inhibitor. Probenecid, sulfinpyrazone and benzbromarone are examples of uric acid excretion promoters. Interleukin-6 (IL-6) has been proposed for use in the treatment of gout as a serum uric acid decreasing agent (see U.S. Pat. No. 6,007,804).

Pseudogout is not a hyperuremic disorder, and involves the deposition of calcium pyrophosphate.

BRIEF SUMMARY OF THE INVENTION

In a first aspect, the invention features a method of treating, inhibiting, or ameliorating metabolic rheumatic disorders associated with hyperuricemia comprising administering to a subject in need an interleukin 1 (IL-1) antagonist to a subject in need thereof. An IL-1 antagonist is a compound capable of blocking or inhibiting the biological action of IL-1, including fusion proteins capable of trapping IL-1, such as an IL-1 "trap". In a preferred embodiment, the IL-1 trap is an IL-1-specific fusion protein comprising two IL-1 receptor components and a multimerizing component, for example, an IL-1 trap described in U.S. Pat. No. 6,927,044, herein specifically incorporated by reference in its entirety. An IL-1 trap fusion protein comprises an IL-1 binding portion of the extracellular domain of human IL-1RAcP, an IL-1 binding portion of the extracellular domain of human IL-1 RI, and a multimerizing component. In a specific embodiment, the IL-1 trap is the fusion protein shown in SEQ ID NO:10 (rilonacept) or a protein having at least 95% identity to the protein of SEQ ID NO:10 and capable of binding and inhibiting IL-1. Use of the IL-1 trap to treat gout offers unexpected advantages relative to the use of prior art IL-1 antagonists for several reasons, including allowing alleviation of gout symptoms with reduced frequency of administration, reduced side effects such as, for example, reduced injection site inflammation or reduced immunogenicity.

In a preferred embodiment, the metabolic rheumatic disorder associated with hyperuricemia is gout. The subject being treated is most preferably a human diagnosed as suffering from gout, for example, chronic acute gout. The method of the invention encompasses preventing or ameliorating gout or hyperuricemia in a human subject suffering therefrom.

In a more specific embodiment, the gout condition being treated is drug-induced gout flares, including flares induced by xanthine oxidase inhibitors such as allopurinol and febuxostat; flares induced by urate oxidase, for example, uricase, rasburicase and pegylated uricase; and flares induced by uricosuric agents, such as probenecid, sulfinpyrazone, benzbromarone, and fenofibrate.

In one example of drug-induced gout, patients treated with a xanthine oxidase inhibitor, a urate oxidase, or a uricosuric agent, are treated with an IL-1 antagonist to reduce the frequency and severity of acute gout flares associated with the initiation of the xanthine oxidase inhibitor, a urate oxidase, or a uricosuric agent therapy. In a specific embodiment, the IL-1 antagonist reduces, inhibits or prevents the occurrence of drug-induced flares by at least about 50%, more preferably 60%, 75% or 80%, relative to not receiving the IL-1 antagonist; in even more specific embodiments, the IL-1 antagonist reduces, inhibits or prevents drug-induced gout flares by about 80% relative to not receiving the IL-1 antagonist. In a specific embodiment, the drug-induced gout flare is associated with initiation of allupurinol or febuxostat therapy.

In a second aspect, the invention features a method of treating, inhibiting, or ameliorating pseudogout, comprising administering to a subject in need an interleukin 1 (IL-1) antagonist to a subject in need thereof.

The methods of the invention includes administration of the IL-1 antagonist by any means known to the art, for example, subcutaneous, intramuscular, intravenous, transdermal administration or oral routes of administration. Preferably, administration is by subcutaneous or intravenous injection or intravenous infusion.

In specific embodiments of the therapeutic method of the invention, the subject is treated with a combination of an IL-1 trap and a second therapeutic agent. The second therapeutic agent an additional IL-1 antagonist and/or co-therapies such as uric acid synthesis inhibitors to inhibit the accumulation of uric acid in the body, for example, allopurinol, uric acid excretion promoters to accelerate the rapid excretion of uric acid accumulated in the body, for example, probenecid, sulfinpyrazone and/or benzbromarone are examples of uric acid excretion promoters; corticosteroids; non-steroidal anti-inflammatory drugs (NSAIDs); and/or cholchicine. Administration of the first and second therapeutic agents may be separately, simultaneously, or sequentially.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Metabolic Rheumatic Disorders Associated with Hyperuricemia

Gout is a group of metabolic rheumatic disorders associated with hyperuricemia and is the most common cause of an inflammatory arthropathy in middle-aged men. Gout is essentially a disorder of urate metabolism. Deposition of urate crystals in hyperuricemic individuals results in acute gout, characterized by agonizing pain and inflammation of rapid onset, most frequently affecting the first metatarsophalangeal joint. Hyperuricemia is associated with an increased risk of developing gout and this increases with the degree and duration of the hyperuricemia.

Treatment of gout aims to relieve pain and inflammation of the acute attack, and reduce the incidence of recurrent attacks. Dietary and pharmacological urate-lowering therapies principally aim to prevent clinical joint damage. Common approaches to the treatment of acute gout are corticosteroids, non-steroidal anti-inflammatory drugs (NSAIDs), and colchicine. The side effects of these drugs, particularly in the frail, elderly population who experience the highest incidence of acute gout, can be serious. An approach to the prevention of recurrent gout is the use of a xanthine oxidase inhibitor, allopurinol. However, allopurinol can have serious side effects such as allopurinol hypersensitivity syndrome (see, for example, Arellano et al. (1993) Ann Pharmacother 27:337-343).

Alternative drugs for preventing gout include the uricosuric agent sulphinpyrazone, limited by its side-effect profile, and benzbromarone and probenecid. Fenofibrate, a drug well known in the treatment of various forms of hyperlipidemia, has been proposed for the treatment of hyperuricemia.

Pseudogout

Pseudogout is a type of arthritis that, as the name implies, can cause symptoms similar to gout, but in reaction to a different type of crystal deposit. Pseudogout, sometimes referred to as calcium pyrophosphate deposition disease, can cause severe episodes of localized pain and swelling resulting in incapacitation for days or weeks. It also can cause more chronic arthritis that mimics osteoarthritis or rheumatoid arthritis. Knees are most often involved but wrists, shoulders, ankles, elbows or hands can be affected. Pseudogout is caused when deposits of calcium pyrophosphate crystals accumulate in a joint.

IL-1 Trap Antagonists

Interleukin-1 (IL-1) traps are multimers of fusion proteins containing IL-1 receptor components and a multimerizing component capable of interacting with the multimerizing component present in another fusion protein to form a higher order structure, such as a dimer. Cytokine traps are a novel extension of the receptor-Fc fusion concept in that they include two distinct receptor components that bind a single cytokine, resulting in the generation of antagonists with dramatically increased affinity over that offered by single component reagents. In fact, the cytokine traps that are described herein are among the most potent cytokine blockers ever described. Briefly, the cytokine traps called IL-1 traps are comprised of the extracellular domain of human IL-1R Type I (IL-1RI) or Type II (IL-1RII) followed by the extracellular domain of human IL-1 Accessory protein (IL-1AcP), followed by a multimerizing component. In a preferred embodiment, the multimerizing component is an immunoglobulin-derived domain, such as, for example, the Fc region of human IgG, including part of the hinge region, the CH2 and CH3 domains. An immunoglobulin-derived domain may be selected from any of the major classes of immunoglobulins, including IgA, IgD, IgE, IgG and IgM, and any subclass or isotype, e.g. IgG1, IgG2, IgG3 and IgG4; IgA-1 and IgA-2. Alternatively, the IL-1 traps are comprised of the extracellular domain of human IL-1AcP, followed by the extracellular domain of human IL-1RI or IL-1RII, followed by a multimerizing component. For a more detailed description of the IL-1 traps, see WO 00/18932, which publication is herein specifically incorporated by reference in its entirety. Preferred IL-1 traps have the amino acid sequence shown in SEQ ID NOs: 2, 4, 6, 8, 10, 12, 14, 16, 18, 20, 22, 24, and 26, or a substantially identical protein at least 95% identity to a sequence of SEQ ID NO:2, 4, 6, 8, 10, 12, 14, 16, 18, 20, 22, 24, or 26, and capable of binding and inhibiting IL1. Most preferably, the IL-1 antagonist is the protein of SEQ ID NO:10 (rilonacept).

In specific embodiments, the IL-1 antagonist comprises an antibody fragment capable of binding IL-1α, IL-1β, IL-1R1 and/or IL-1RAcp, or a fragment thereof. The preferred embodiment would be an antagonist of IL-1β. One embodiment of an IL-1 antagonist comprising one or more antibody fragments, for example, single chain Fv (scFv), is described in U.S. Pat. No. 6,472,179, which publication is herein specifically incorporated by reference in its entirety. In all of the IL-1 antagonist embodiments comprising one or more antibody-derived components specific for IL-1 or an IL-1 receptor, the components may be arranged in a variety of configurations, e.g., a IL-1 receptor component(s)-scFv(s)-multimerizing component; IL-1 receptor component(s)-multimerizing component-scFv(s); scFv(s)-IL-1 receptor component(s)-multimerizing component, ScFv-ScFv-Fc, etc., so long as the molecule or multimer is capable of inhibiting the biological activity of IL-1.

Treatment Population

The method of the instant invention provides treatment of pseudogout and metabolic rheumatic disorders associated with hyperuricemia to human patients suffering therefrom. The treatment population is thus human subjects diagnosed as suffering from pseudogout, gout or hyperuricemia. The invention encompasses the treatment of a human subject at risk of suffering from a recurrent gout episode or for developing gout or pseudogout.

The invention also encompasses treating a population of patients with drug-induced gout flares, including flares induced by gout therapeutics such as xanthine oxidase inhibitors, such as allopurinol and febuxostat; flares induced by urate oxidase, for example, uricase, rasburicase and pegylated uricase; and flares induced by uricosuric agents, such as probenecid, sulfinpyrazone, benzbromarone, and fenofibrate. By "drug-induced" gout flare is meant occurrence of or increased incidence of a gout flare associated with initiation of therapy to treat gout and/or administration of a therapeutic agent for the treatment of gout, for example, initiation of therapy with a xanthine oxidase inhibitor, urate oxidase, or a uricosuric agent. A gout flare is "associated" with initiation of gout therapy when the flare occurs contemporaneously or following at least a first administration of a therapeutic agent for the treatment of gout.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects).

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, commercial skin substitutes or angioplasty balloons or stents.

An initial dose may be followed by subsequent doses at a frequency of daily, weekly, biweekly, monthly or even less frequently. An initial dose, preferably administered subcutaneously or intravenously, may range from about 80 mg to about 500 mg of IL-1 antagonist, and subsequent doses may range from about 40 mg to about 250 mg of IL-1 antagonist.

Combination Therapies

In numerous embodiments, the IL-1 antagonists of the present invention may be administered in combination with one or more additional compounds or therapies. Combination therapy may be simultaneous or sequential. The IL-1 traps of the invention may be combined with, for example, TNF-inhibiting agents such as etanercept (ENBREL®, Amgen), infliximab (REMICADE®, Centocor), HUMIRA® (Abbott). Combination therapy may also include treatment with drugs currently used for the treatment or prevention of gout, including corticosteroids, non-steroidal anti-inflammatory drugs (NSAIDs); colchicine; xanthine oxidase inhibitors such as allopurinol and febuxostat; uricosuric agents such as sulphinpyrazone, benzbromarone and probenecid; and fenofibrate; and urate oxidase inhibitors such as uricase, rasburicase and pegylated uricase. Preferred co-therapeutics include NSAIDs, steroids and/or cholchicine.

Pharmaceutical Compositions

The present invention also provides pharmaceutical compositions. Such compositions comprise a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention which will be effective in the treatment of delayed-type hypersensitivity can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

A Phase I/II, Placebo Controlled Pilot Study of the Safety, Tolerability, and Clinical Activity of Rilonacept for the Treatment of Chronic Active Gout Gout is a common disease with increasing incidence. There are approximately 5MM Americans with gout. Medical needs are not fully met; a large number of individuals are either intolerant or not good candidates for current therapeutic or prophylactic strategies. This study explores the activity of rilonacept at one end of the gout spectrum: chronic active (refractory) gout. Results from this study may or may not be indicative of rilonacept's potential utility in acute active gout or in the prevention of gout flares; however, activity in this situation suggests potential benefit. The chronic active (refractory) gout population, while small, represents a true situation of medical need.

Primary Objective: To assess the safety of rilonacept in subjects with chronic, active gout, having at least one joint continuously inflamed.

Secondary Objectives: (1) To compare within subject changes in self-reported pain score (VAS) during the placebo run-in phase with the active treatment phase; (2) to assess the changes in the Subject and Physician Global Assessments during the placebo run-in and active treatment phases; (3) to assess the effect of rilonacept on C-reactive protein (CRP) and erythrocyte sedimentation rate (ESR) in subjects with chronic active gout.

Study Arms and Cohorts: Subjects are screened at Day −7; a two-week single blind placebo run-in begins at the Baseline visit (2×2 ml of placebo for rilonacept SQ); Single blind rilonacept 320 mg is administered subcutaneously at the Week 2 visit and then subjects self-inject 160 mg/week at home. Visits occur every two weeks through Week 8. PPD skin test, CXR, and inclusion/exclusion criteria are assessed at the Screening visit. Self-injection technique is taught at Screening and Baseline. Laboratory sample collections occur at Screening, Baseline, Weeks 2, 4, and 8. A follow-up visit occurs at Week 14.

Sample Size and Number of Sites: N=5 from up to 5 sites in the U.S.

Drug Supply: Placebo: 5 subjects×2 vials=10 vials+30% overage=13 vials; Rilonacept: 5 subjects×8 vials=48 vials+30% overage=66 vials, 3 vials per kit.

Subject Eligibility Criteria. Inclusion Criteria: (1) Male or female=21 years; (2) Chronis, active monoarticular or polyarticular gout (=1 continuously inflamed joint due to gout, ±tophi); (3) VAS 10-point pain scale score of =3 (i.e., moderate or greater) due to joint pain/inflammation; (4) subjects for whom standard therapies are ineffective or associated with risks related to side effects.

Exclusion Criteria: (1) Organ transplant recipient; (2) current active infection; (3) serum creatinine<2.5 mg/dL; (4) other arthritic condition that could interfere with evaluations.

Primary Endpoint: Tolerability and safety profile of rilonacept.

Secondary Endpoints: (1) The change from Baseline to Week 8 in subject's pain score (10 cm VAS scale); (2) the change from Baseline to Week 8 in the Subject's Global Assessment; (3) the change from Baseline to Week 8 in the Physician's Global Assessment; (4) the change from Baseline to Week 8 in ESR and CRP.

Example 2

Safety of Rilonacept in Subjects with Chronic Active Gouty Arthritis

A 14 week, multi-center, non-randomized, single-blind, placebo-controlled, monosequence crossover study of rilonacept in subjects with chronic, active monoarticular or polyarticular gouty arthritis. Subjects receive 2 weeks of single-blind placebo followed by a loading dose of subcutaneous injections of 320 mg rilonacept, followed by weekly subcutaneous injections for 5 weeks of 160 mg rilonacept. Study Population. The study population included adult subjects (at least 18 years of age, male or female) with chronic, active monoarticular or polyarticular gouty arthritis diagnosed by a physician for at least 6 months with at least one continuously inflamed joint (self-reported or otherwise) for =4 weeks, a diagnosis of gout based on a history of the presence of crystals in the synovial fluid analysis, chronically elevated serum uric acid, and/or tophi; a visual analogue scale increment pain scale score of at least 3 due to joint pain/inflammation at both the Screening and Baseline Visits, and subjects for whom standard therapies for gout are less than effective or are associated with risks related to side effects.

Study Design. This study was a 14-week, multi-center, non-randomized, single-blind, placebo-controlled, monosequence crossover study of IL-1 trap (rilonacept) in subjects with chronic, active monoarticular or polyarticular gouty arthritis. Subjects received 2 weeks of single-blind placebo followed by a loading dose of subcutaneous injections of 320 mg rilonacept, followed by weekly subcutaneous injections for 5 weeks of 160 mg rilonacept. The study was conducted in approximately 12 sites in the U.S. This study includes a monosequence crossover design for the enrolled subjects: Treatment 1: Placebo injections for two weeks; Treatment 2: Injections of rilonacept for six weeks. Descriptive statistics was used to evaluate safety and efficacy of rilonacept in gout. Approximately 10 subjects were enrolled to receive placebo (2 weeks) and rilonacept (6 weeks) administered subcutaneously. Subjects received a total of two doses of placebo (on study days 0 and 7) and six doses of rilonacept on Days 14, 21, 28, 35, 42, and 49 during the study. Dose escalation was not allowed. Subjects were evaluated for efficacy and safety on a regular basis with clinical observations and laboratory measurements including anti-rilonacept antibodies, hs-CRP and ESR. The overall structure of the study included the following periods: Screening period: Screening procedures occurred within 7 days of start of study and included obtaining informed consent and evaluations to determine eligibility for study participation. Baseline: At the baseline visit (day 0), eligibility was confirmed, and the subject enrolled. Baseline assessments were made. The first injection of placebo was administered, and a vial of placebo dispensed. Placebo Treatment period: During the treatment period (Day 0 through Week 2), patients received placebo study medication, efficacy assessments were taken; safety and tolerability assessments were taken, including urine and blood samples for clinical laboratory testing. Active Treatment period: During the treatment period (Week 2 through Week 8), patients received active study medication, efficacy assessments were taken; safety and tolerability assessments were taken, including urine and blood samples for clinical laboratory testing. Blood samples were collected for biomarkers, IL-1 trap (rilonacept) plasma levels, and rilonacept antibodies. Follow-up: At Week 14, vital signs, bodyweight, adverse events, and concomitant medications assessments were taken. Blood samples were collected for biomarkers, rilonacept plasma levels, and rilonacept antibodies. The results are shown in Table 1. The first column lists the parameters assessed; column 2 (placebo response) compares the parameter measurements obtained at Week 2 with those measured at Day 0; column 3 (response of rilonacept) compares the parameter measurements obtained at Week 8 with those of Week 2; and column 4 (effect of withdrawal from treatment with rilonacept) compares the parameter measurements obtained at Week 14 with those obtained at Week 2.

Results. During treatment with placebo, there was no apparent trend toward improvement in any clinical parameter nor in CRP. Also, during treatment with placebo, there is no evidence of improvement. At the end of treatment with rilonacept, the proportion of responders is significantly better than a placebo response of 10%, regardless of how response was defined ($p<0.01$). Also, there was a significant reduction in patient's self-reported pain ($p=0.02$). When treatment with rilonacept was withdrawn, the trends toward efficacy waned and pain returned. These results suggest that placebo response is minimal, and reduction in pain is not observed until treatment with rilonacept is administered.

TABLE 1

| | Placebo Response | Rilonacept Response | | | Effects of Withdrawal from Treatment with Rilonacept |
|---|---|---|---|---|---|
| Assessment | Change Day 0-week 2 | Change Week 2-4 | Change week 2-4 | Change week 2-8 | Change week 8-14 |
| Subject's Assessment of Pain | 0.96 | 0.046 | 0.07 | 0.02 | 0.07 |
| Physician's Global Assessment | 0.09 | 0.4 | 0.8 | 0.2 | 0.02 |
| Subject's Global Assessment | 1.0 | 0.07 | 0.14 | 0.06 | 0.02 |
| Number of Affected Joints | 0.3 | 0.7 | 0.9 | 0.099 | 0.95 |
| Symptom-Adjusted Scores for Affected Joints (maximum of 3 per joint) | 0.2 | 0.7 | 0.8 | 0.04 | 0.3 |
| Severity-and-Symptom-Adjusted Scores for Affected Joints (maximum of 9 per joint) | 0.2 | 0.2 | 0.8 | 0.04 | 0.14 |
| Change from Baseline CRP | 0.5 | 0.002 | 0.004 | 0.004 | 0.04 |

Example 3

Effectiveness of IL-1 Antagonist for Prevention of Gout Flares During Initiation of Allopurinol Therapy A multi-center, randomized, double-blind, placebo-controlled study in subjects with intercritical gout was conducted. 83 subjects were enrolled and treated with allopurinol orally once a day beginning on Day 1. Subjects were randomized in a 1:1 ratio to receive 160 mg rilonacept subcutaneously once a week or a placebo subcutaneously once a week for 16 weeks. Subjects received a loading dose on Day 1 (Baseline Visit) of rilonacept (320 mg given as two vials of 160 mg) or placebo (given in two equal volumes)(volumes 2 ml each) administered as subcutaneous injections.

Subjects in both treatment arms were started on a daily dose of 300 mg allopurinol on Day 1. The allopurinol dose was adjusted by 100 mg increments monthly to titrate subjects until they attained a serum uric acid level of less than 6 mg/dL. The maximum dose of allopurinol was 800 mg per day. For subjects with impaired renal function, the initial dose of allopurinol was adjusted based on the estimated creatinine clearance according to the Cockroft-Gault formula for estimating creatinine clearance.

Subjects would return to the clinic every 4 weeks for 16 weeks for study related procedures. Sites would call subjects every 2 weeks between visits for a brief review of their clinical status. A Safety Follow-up visit would occur 42 days after the last dose of study drug.

Subjects were instructed to call the study site upon first symptoms of a self-reported gout flare. A daily diary capturing pain, global well-being and symptoms of gout was completed by the subject starting on Day 1 of the flare until the resolution of all flare symptoms. Day 1 of the flare was defined as the onset of pain in any gouty joint and the end of the flare was defined as the day all pain in all joints resolved. All gout flares that occurred during the study from Baseline through the Terminal Visit (Visit 6) were followed to completion.

Screening period. Screening procedures occurred within 2 weeks of start of study and included obtaining informed consent and evaluations to determine eligibility for study participation.

Baseline. At the baseline visit (day 1), eligibility was confirmed, and the subject randomized. Baseline assessments were made. The first administration (2 injections) of either 160 mg rilonacept (total loading dose of 320 mg rilonacept) or placebo was administered, and vials of the study medication dispensed. Subjects also received 300 mg allopurinol.

Treatment period. During the treatment period (Day 1 through Week 16), subjects received study medication (including daily allopurinol, adjusted as appropriate), efficacy assessments were taken; safety and tolerability assessments were taken, including urine and blood samples for clinical laboratory testing. Primary and secondary efficacy endpoints were measured at Week 12, but treatment continued through Week 16. All safety variables were summarized with time periods from Day 1 of study medicine to last dose date plus 42 days.

Follow-up. At Week 22, subject diaries were reviewed; vital signs, adverse events, and concomitant medications assessments were taken. Blood samples were collected for clinical laboratory assessments, rilonacept plasma levels and rilonacept antibodies assessments.

Primary efficacy variables. The primary efficacy variable was the mean number of gout flares from Day 1 to Week 12. The variable was calculated for each subject as number of flares observed from Day 1 to Week 12. For dropouts, only numbers of flares that occurred during the treatment period (defined as termination date-randomization date+1) were counted.

Secondary efficacy variables. (1). The proportion of subjects with one or more gout flares from Day 1 to Week 12. (2). The mean number of gout flares per month from Day 1 to Week 12. The variable was calculated for each subject as: Mean number of flares per month=(number of flares observed from Day 1 to Week 12)/(number of days subject was in study/28 days). (3). The mean number of gout flare days from Day 1 to Week 12. The variable for each subject was calculated as number of gout flares days from Day 1 to Week 12. Subjects with flares that started before the Week 12 visit and ended after the Week 12 visit included only days up to the Week 12 visit. (4). The mean number of gout flare days per month from Day 1 to Week 12. The mean number of gout flare days per month was calculated for each subject: Mean number of gout flares days per month from Day 1 to Week 12=(Number of flares days from Day 1 to Week 12)/(Number of days subject was in the study/28 days). Subjects with flares that started before the Week 12 visit and ended after the Week 12 visit included only days up to the Week 12 visit. (5). The mean number of days with the subject's pain score of 5 or more (from daily dairy) from Day 1 to Week 12. This was calculated for each subject as number of days with the subject's pain score 5 or more observed from Day 1 to Week 12. (6). The mean number of days per month with the subject's pain score of 5 or more (from daily dairy) from Day 1 to Week 12. This was calculated for each subject as: mean number of days per month with the subject's pain score 5 or more from Day 1 to Week 12=(Number of days with the subject's pain score of 5 or more observed)/(Number of days subject was in the study/28 days).

Exploratory Efficacy Variables. Exploratory variables included time to first gout flare, percentage of subjects with usage, and duration of NSAIDS and glucocorticoids during study, proportion of subjects with uric acid levels less than 6 mg/dL by visit, and percentage of total gout flares by number of visits. The time period for all these variables was from Day 1 to Week 12.

Results are shown in Tables 2 and 3. Rilonacept achieved a dramatic 81% reduction in gout flares, from 0.79 to 0.15 (Table 2; p=0.0006). [1]P-value is based on the two-sample t-test; [2]Gout-Free-Flare: no gout flare during time interval; [3]P-value based on Fisher's exact test.

TABLE 2

| Time Interval | Rilonacept | Placebo | P-value |
|---|---|---|---|
| Day 1 to Week 12 | | | |
| Mean Number of Gout Flares | 0.15 ± 0.358 (n = 41) | 0.79 ± 1.071 (n = 42) | 0.0006[1] |

TABLE 3

| Time Interval | Rilonacept | Placebo | P-value[3] |
|---|---|---|---|
| Day 1 to Week 12 | | | |
| Subjects Gout-Flare-Free[2] | 85.4% (n = 35) | 54.8% (n = 23) | 0.0037 |
| Subjects with ≧ Gout Flare | 14.6% (n = 6) | 45.2% (n = 19) | |

What is claimed is:

1. A method of reducing the occurrence of gout flares in a subject, said method comprising administering to the subject a course of treatment comprising an interleukin-1 (IL-1) antagonist once per week, wherein the subject is treated concurrently with a uric acid synthesis inhibitor.

2. The method of claim 1, wherein the uric acid synthesis inhibitor is allopurinol.

3. The method of claim 1, wherein the IL-1 antagonist is an IL-1 trap.

4. The method of claim 3, wherein the IL-1 trap is rilonacept.

5. The method of claim 2, wherein the IL-1 antagonist is an IL-1 trap.

6. The method of claim 5, wherein the IL-1 trap is rilonacept.

7. The method of claim 1, wherein the IL-1 antagonist is administered at an initial dose of about 80 mg to about 500 mg on the first day of treatment.

8. The method of claim 7, wherein the IL-1 antagonist is an IL-1 trap.

9. The method of claim 8, wherein the IL-1 trap is rilonacept.

10. The method of claim 9, wherein the rilonacept is administered at an initial dose of 320 mg on the first day of treatment.

11. The method of claim 7, wherein the IL-1 antagonist is administered at subsequent doses of about 40 mg to about 250 mg.

12. The method of claim 11, wherein the IL-1 antagonist is an IL-1 trap.

13. The method of claim 12, wherein the IL-1 trap is rilonacept.

14. The method of claim 13, wherein the rilonacept is administered at subsequent doses of 160 mg.

15. The method of claim 11, wherein the uric acid synthesis inhibitor is allopurinol.

16. The method of claim 12, wherein the uric acid synthesis inhibitor is allopurinol.

17. The method of claim 13, wherein the uric acid synthesis inhibitor is allopurinol.

18. The method of claim 14, wherein the uric acid synthesis inhibitor is allopurinol.

19. The method of claim 1, wherein the course of treatment is administered for 16 weeks.

20. The method of claim 1, wherein the IL-1 antagonist is administered subcutaneously.

* * * * *